US010512597B2

(12) United States Patent
Pilch et al.

(10) Patent No.: US 10,512,597 B2
(45) Date of Patent: Dec. 24, 2019

(54) CONTROLLED SURFACE GELLING OF MUCOADHESIVE POLYMERS ON ORAL MUCOSA

(75) Inventors: Shira Pilch, Highland Park, NJ (US); James Gerard Masters, Ringoes, NJ (US); Rensl Dillon, Ewing, NJ (US); David Benedict Viscio, Prescott Valley, AZ (US)

(73) Assignee: Colgate-Palmolive Company, New York, NY (US)

( * ) Notice: Subject to any disclaimer, the term of this patent is extended or adjusted under 35 U.S.C. 154(b) by 1772 days.

(21) Appl. No.: 11/850,886

(22) Filed: Sep. 6, 2007

(65) Prior Publication Data
US 2009/0068259 A1    Mar. 12, 2009

(51) Int. Cl.
*A61K 8/11*   (2006.01)
*A61K 8/19*   (2006.01)
*A61K 8/73*   (2006.01)
*A61Q 11/00*  (2006.01)

(52) U.S. Cl.
CPC ............... *A61K 8/11* (2013.01); *A61K 8/19* (2013.01); *A61K 8/73* (2013.01); *A61Q 11/00* (2013.01); *A61K 2800/412* (2013.01)

(58) Field of Classification Search
CPC ...... A61K 2800/412; A61K 8/11; A61K 8/19; A61K 8/73; A61Q 11/00
See application file for complete search history.

(56) References Cited

U.S. PATENT DOCUMENTS

| | | | | |
|---|---|---|---|---|
| 4,071,614 A * | 1/1978 | Grimm, III | ............ | A61K 8/11 424/10.32 |
| 4,980,154 A * | 12/1990 | Gordon | ............ | 424/53 |
| 5,330,749 A * | 7/1994 | Giacin | ............ | A61K 8/19 424/49 |
| 5,571,502 A * | 11/1996 | Winston | ............ | A61K 8/19 424/49 |
| 5,885,552 A | 3/1999 | Causton | | |
| 5,976,507 A * | 11/1999 | Wong | ............ | A61K 8/11 424/451 |
| 6,159,459 A * | 12/2000 | Hunter et al. | ............ | 424/78.08 |
| 6,258,343 B1 * | 7/2001 | Kiczek et al. | ............ | 424/52 |
| 6,669,929 B1 | 12/2003 | Boyd et al. | | |
| 2002/0013331 A1 * | 1/2002 | Williams et al. | ............ | 514/282 |
| 2005/0196351 A1 | 9/2005 | Soshinsky | | |
| 2006/0019016 A1 | 1/2006 | Torcatis | | |
| 2007/0128285 A1 | 6/2007 | Jin et al. | | |
| 2008/0020065 A1 * | 1/2008 | Cherukuri | ............ | 424/687 |

FOREIGN PATENT DOCUMENTS

| | | |
|---|---|---|
| EP | 0 745 385 A | 12/1996 |
| WO | 9959535 A1 | 11/1999 |
| WO | 2007012981 A | 2/2007 |
| WO | WO 2007/012981 * | 2/2007 |

OTHER PUBLICATIONS

International Search Report dated Jan. 30, 2009.

* cited by examiner

*Primary Examiner* — Snigdha Maewall

(57) ABSTRACT

The present invention relates to an oral composition and method for alleviating the symptoms associated with xerostomia using encapsulated cation-releasing compounds formulated either intimately together or in separate compartments in a composition containing cation-sensitive mucoadhesive polymers.

6 Claims, No Drawings

CONTROLLED SURFACE GELLING OF MUCOADHESIVE POLYMERS ON ORAL MUCOSA

BACKGROUND OF THE INVENTION

Xerostomia, commonly known as "dry mouth," is a condition in which the salivary glands do not produce sufficient quantities of saliva. Normally, mucous forms a continuous protective layer in the nose, mouth and throat. A patient suffering from xerostomia not only has decreased fluid in the mouth, but also an insufficient quantity of mucoproteins and mucopolysaccharides to hold fluid in contact with the cells and create a barrier to irritation and infection. This causes discomfort which can in some cases be quite severe. Without saliva, the mouth burns and the throat and tongue can undergo radical changes. Teeth can decay rapidly and the tongue can become smooth, cracked and vulnerable to infection.

Symptoms of mild xerostomia can be somewhat alleviated by the consumption of fluids, chewing gums, oral sprays, mouthwashes, hard candies and throat lozenges. Artificial saliva and salivary substitutes have also been proposed as palliative treatments for the symptoms of xerostomia, which preparations have physical and chemical properties that simulate those of natural (human) saliva. Examples of artificial salivas include compositions which contain ions that mimic those found in natural saliva, glycerin, as well as carboxymethylcellulose-based preparations to provide the proper level of viscosity. Fluoride ions are sometimes included to these preparations to prevent demineralization of tooth enamel. Nevertheless, these compositions have not found wide acceptance as many patients find that such preparations are irritating or distasteful and that their lubricating effect is of relatively short duration.

BRIEF SUMMARY OF THE INVENTION

The present invention relates to an oral composition and method for alleviating the symptoms associated with xerostomia using encapsulated cation-releasing compounds formulated either intimately together or in separate compartments in a composition containing cation-sensitive mucoadhesive polymers.

In one embodiment, the oral composition includes a cation-sensitive mucoadhesive polymer and a cation-releasing compound, wherein the cation-releasing compound is encapsulated in a water-insoluble, rupturable capsule.

In one embodiment, the oral composition includes a first component having a cation-sensitive mucoadhesive polymer and a second component having an encapsulated cation-releasing compound, the first and second components being maintained separate from each other until dispensed and combined for application to the oral cavity.

In one embodiment, a method for reducing dryness in an oral cavity includes the steps of delivering into the oral cavity a composition containing a mucoadhesive polymer and water-insoluble capsules containing a cation-releasing compound, releasing the cation-releasing compound from the capsules in the oral cavity, releasing cations from the cation-releasing compound, exposing the Mucoadhesive polymer to the cations, and adhering the mucoadhesive polymer to oral surfaces in the oral cavity.

DETAILED DESCRIPTION OF THE INVENTION

Unless otherwise specified, all percentages and amounts expressed herein and elsewhere in the specification should be understood to refer to percentages by weight. Also, the term "about," when used in reference to a range of values, should be understood to modify either value in the range, or to both values in the range.

As used throughout, ranges are used as shorthand for describing each and every value that is within the range. Any value within the range can be selected as the terminus of the range.

In addition, all references cited herein are hereby incorporated by reference in their entireties. In the event of a conflict in a definition in the present disclosure and that of a cited reference, the present disclosure controls.

Monovalent cations, such as Na+, and K+ and divalent cations, such as Ca2+ and Mg2+ trigger the gelation process and/or enhance the structure of certain mucoadhesive polymer gels. Furthermore, the cations can act as ionic bridges between these cation-sensitive mucoadhesive polymers and the oral mucosa, providing stronger adhesion of the mucoadhesive polymer to the oral surfaces. By exposing these cation-sensitive mucoadhesive polymers to the cations in the oral cavity, the gelling of the mucoadhesive polymers is facilitated and their adhesion to the oral surfaces is enhanced.

Examples of compositions and methods that have been used to alleviate the symptoms associated with dry mouth are described in U.S. Pat. Nos. 5,658,554, 6,159,459, and 7,198,779, which are each incorporated herein by reference in their entireties.

The present invention overcomes the problems and disadvantages associated with current treatments for xerostomia by using sterically entrapped or encapsulated cation-releasing compounds formulated either intimately together or in a separate compartment in a low ionic strength composition containing cation-sensitive mucoadhesive polymers, that when delivered from oral vehicles such as mouthwashes, sprays and toothpastes, the shear imposed during use ruptures the encapsulation and releases the soluble cations from the cation-releasing compounds, allowing the cations to interact with the mucoadhesive polymers to increase surface adhesion. As mentioned above, the cations facilitate the gelling of the cation-sensitive mucoadhesive polymers and their interaction with the outer layers of mucin, providing a strong viscoelastic layer which acts as a lubricating moisture barrier and in turn provides a long-lived lubricating moisture barrier and protective coating that may help alleviate the symptoms of xerostomia.

In certain embodiments, a composition in accordance with the present invention includes a cation-sensitive mucoadhesive polymer and a cation-releasing compound, wherein the cation-releasing compound is encapsulated in a rupturable capsule.

Examples of mucoadhesive polymer materials that are sensitive to cation exposure include gellan gum and carrageenan. Gellan gum is a hydrocolloid produced via the fermentation process of carbohydrate by microorganisms. The molecular structure of gellan gum is a straight chain based on repeating glucose, rhamnose and glucuronic acid units. Carrageenan is a cell wall hydrocolloid found in certain species of seaweeds belonging to red algae and is composed of repeating units of galactose and 3,6-anhydrogalactose with sulfate esters in varying amount and location depending on the type of carrageenan. Any form of carrageenan may be use, including K-, L-, and/or λ-. Both gellan gum and carrageenan exhibit enhanced gel structure with increased cation concentrations (0.01-1%). Other examples of cation-sensitive mucoadhesive polymers include alginates and pectin.

In one embodiment, a cation-sensitive mucoadhesive polymer for use in the present invention includes a low acyl gellan gum that is marketed by CP Kelco as Kelcogel® CG at an amount of about 0.025% to about 2.5% by weight. In another embodiment, a mucoadhesive polymer for use in the present invention is iota or kappa carrageenan or a mixture thereof at an amount of about 0.1% to about 1% by weight.

It should be noted that any polymeric materials useable in oral care preparations which exhibit gelling behavior in the presence of cations can be used in the present invention.

Cation-releasing compounds that may be used in accordance with the present invention include salts, such as calcium salts, sodium salts, and metal salts. In certain embodiments, the cation-releasing compound includes soluble divalent salts. A cation-releasing compound useable in the present invention is calcium chloride ($CaCl_2$), which releases divalent $Ca2+$ cations when dissolved. Additional cation-releasing compounds that may be used in the present invention include other non-toxic soluble calcium salts such as calcium acetate, calcium butylate, calcium citrate, calcium lactate, and calcium salicylate, and non-toxic soluble magnesium salts, such as, magnesium sulfate, and magnesium chloride. Other metal salts may be suitable, such as tin salts, iron salts, copper salts, gold or silver salts, and/or titanium salts.

By encapsulating a cation-releasing compound in a capsule or shell, the cation-releasing compound can be maintained substantially separate (e.g. sequestered) from the other ingredients of the oral composition until subsequently being released when the capsules rupture during application to oral surfaces by the consumer. When delivered from an oral care vehicle, such as a mouthwash, spray or toothpaste, the mechanical and/or shear forces imposed on the composition, for example, during the spraying onto the oral surfaces or during the course of brushing, ruptures the capsules and releases the soluble cations, allowing the released cations to interact with the cation-sensitive mucoadhesive polymers to facilitate gelation and adhesion of the mucoadhesive polymers to the oral surfaces. Encapsulation of the cation-releasing compounds prevents exposure of the mucoadhesive polymers to the cations prior to use by the consumer, such as during manufacture and storage of the oral composition, which would otherwise result in premature gelation and decreased adhesion of the mucoadhesive polymer to the oral surfaces.

Encapsulation materials may be water soluble or insoluble. Materials that may be used for encapsulating the cation-releasing compounds in accordance with the present invention include silicone, gelatin, amphipilic diblock copolymers, phospholipids, neutral block copolymers, polyethylene oxide polyethylene, poly lactic-co-glycolic acid (PLGA), alkyl cellulose polymers such as ethyl cellulose, and other cellulosic polymers. Other encapsulation materials that may be useful in the present invention include synthetic organic plastic materials such as phenol formaldehydes, vinyl chloride polymers, polyethylene, polypropylene, polyurethanes, ABS resins, and waxes.

Methods which may be used for encapsulating the cation-releasing compounds of the present invention are described in U.S. Pat. Nos. 5,976,507 and 6,258,343, which are each incorporated herein by reference in their entireties. U.S. Pat. No. 5,976,507 describes dentifrice compositions and methods for preparing the same wherein at least one active ingredient, such as a calcium salt, is encapsulated in a plasticized alkyl cellulose polymer shell. U.S. Pat. No. 6,258,343 describes an improved method for encapsulating active dental ingredients, such as a calcium salt, in an alkyl cellulosic polymer matrix.

Other materials and methods for encapsulating ingredients in oral compositions known in the art may also be useful in the present invention. For example, U.S. Pat. Nos. 3,957,964, 3,929,988, 4,071,614, 4,220,552, 4,348,378, and 4,376,762, which are each incorporated herein by reference in their entireties, describe oral compositions containing ingredients such as flavors and dyes that are encapsulated in rupturable, water-insoluble capsules.

The oral composition of the present invention containing encapsulated cation-releasing compound and mucoadhesive polymers may be administered orally in an acceptable vehicle in liquid or paste form. The oral composition of the present invention may be delivered, for example, as a mouthwash, spray, or toothpaste.

A composition in accordance with the present invention may be prepared by adding the encapsulated cation-releasing compounds and cation-sensitive mucoadhesive polymers to an aqueous vehicle (e.g., for a mouthwash or spray) or dentifrice (e.g., a toothpaste) containing one or more of the following: flavoring agents, surfactants, humectants, sweeteners, preservatives, thickeners, and polishing agents. Other ingredients such as salivary stimulants may also be included to assist in alleviating the symptoms of xerostomia such as, for example, methyl vannillyl nonenamide, gengerol, zingagole, and shoagole.

Examples of flavoring agents useful in the preparation of a mouthwash or spray in accordance with the present invention, which may be included in an amount of about 0.5% to about 2% by weight, include essential oils as well as various flavoring aldehydes, esters, alcohols, and similar materials. Examples of the essential oils include oils of spearmint, peppermint, wintergreen, sassafras clove, sage, eucalyptus, marjoram, cinnamon, lemon, lime, grapefruit, and orange.

Examples of surfactants useful in the preparation of a mouthwash or spray in accordance with the present invention include non-ionic organic surface active polymers such as polyoxyethylene-polyoxypropylene block copolymers such as Pluronic 108 and Pluronic F-127 marketed by BASF. Pluronic 108 has a molecular weight of 3200 and contains 80% of the hydrophilic polyoxyethylene moiety and Pluronic F127 has a molecular weight of 4000 and contains 70% polyoxyethylene. The surfactants assist in achieving thorough and complete dispersion of ingredients throughout the oral cavity and render the compositions more cosmetically acceptable. Non-ionic surfactants also help maintain the flavoring agents in solution by solubilizing the flavor oils. A surfactant may be included in an amount of about 0.25% to about 3% by weight.

Examples of surfactants useful in the preparation of a dentifrice in accordance with the present invention include water-soluble salts of higher fatty acid monoglyceride monosulfates, such as the sodium salt of the monosulfated monoglyceride of hydrogenated coconut oil fatty acids, cocamidopropyl betaine, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine. The surfactants may be used in accordance with the present invention to achieve increased prophylactic action and render the instant compositions more cosmetically acceptable, and are typically present in the dentifrice composition in an amount of about 0.3 to about 5% by weight, preferably about 0.5 to about 2% by weight.

Examples of humectants useful in the preparation of a mouthwash or spray in accordance with the present invention include trimethyglycine, glycerin, sorbitol, xylitol, polyethylene glycol of molecular weight of about 400 to about 2000 or a mixture thereof, which may be included in an amount of about 10% to about 30% by weight or up to about 70% by weight.

Examples of humectants useful in the preparation of a dentifrice in accordance with the present invention include trimethyglycine, glycerin, sorbitol, polyethylene glycol, polypropylene glycol, mannitol, xylitol or a mixture thereof, which may be included in an amount greater than about 20% by weight and preferably about 3% to about 70% by weight.

Examples of sweeteners useful in the preparation of a mouthwash or spray in accordance with the present invention include saccharin, sucralose, or a mixture thereof, which may be included in an amount of about 0.01% to about 1% by weight.

Examples of sweeteners useful in the preparation of a dentifrice in accordance with the present invention include aspartame, saccharin, sucralose, or a mixture thereof, which may be included in amount of about 0.1% to about 2% by weight.

Examples of preservatives useful in the preparation of a mouthwash or spray in accordance with the present invention include benzoic acid, sodium benzoate, cetylpyridinium chloride, parabens or a mixture thereof, which may be included in an amount of about 0.1% to about 2% weight.

Additional ingredients useful in the preparation of a composition in accordance with the present invention include salivary stimulant compounds such as citric acid, ascorbic acid or xylitol, which may be included in an amount of about 0.25 to about 10% by weight. Other ingredients known in the art such as whitening agents, botanical compounds, antibacterial agents, and colorants may also be included.

Examples of thickening agents useful in the preparation of a dentifrice in accordance with the present invention include guar gum, carboxymethyl cellulose and polyoxyethylene polyoxypropylene glycol block copolymers and xanthan gum. Other thickening agents that may be useful in accordance with the present invention include carob bean gum, hydroxymethyl cellulose, and hydroxypropyl cellulose. The thickening agents may be included in an amount of about 0.05% to about 5% by weight, which amount is sufficient to form a semi-solid, extrudable, shape retaining product.

Examples of polishing agents useful in the preparation of a dentifrice in accordance with the present invention include silica, colloidal silica, calcined alumina, sodium bicarbonate, sodium metaphosphate, calcium carbonate, dicalcium phosphate, tricalcium phosphate and calcium pyrophosphate. The polishing agent may be included in an amount of about 1% to about 50% by weight.

Other ingredients known in the art may be included in a composition of the present invention, including antibacterial agents such as triclosan, chlorhexidine, desensitizers such as potassium nitrate, and potassium citrate, whitening agents such as hydrogen peroxide, calcium peroxide and urea peroxide, antitartar agents, preservatives, silicones, dyes, coloring agents, and botanical compounds.

A composition in accordance with the present invention may include a first component having a cation-sensitive mucoadhesive polymer and a second component having a cation-releasing compound which may or may not be encapsulated, the first and second components being maintained separate from each other until dispensed and combined for application to the oral cavity.

For example, a toothpaste composition containing a cation-sensitive mucoadhesive polymer(s) and encapsulated cation-releasing compound(s) in accordance with the present invention may be formulated as a multi-component toothpaste in separate compartments in order to further prevent premature exposure of the mucoadhesive polymer to the cations during storage. In this embodiment, the oral composition may be packaged in a suitable dispensing container in which the mucoadhesive polymer and the encapsulated cation-releasing compounds are maintained physically separated, but from which the separated components may be dispensed synchronously by the consumer to combine the components at the time of use. An example of such a container is a two compartment dispensing container, such as a pump or tube, having collapsible sidewalls, as disclosed in U.S. Pat. Nos. 4,487,757 and 4,687,663, which are each incorporated herein by reference in their entireties. The container body is formed from a collapsible plastic web and is provided with a partition within the container body defining separate compartments in which the physically separated components are stored and from which they are dispensed through a suitable dispensing outlet.

A method for reducing or preventing dry mouth in an oral cavity in accordance with the present invention may include the steps of delivering into the oral cavity a composition containing a mucoadhesive polymer and water-insoluble capsules containing a cation-releasing compound, releasing the cation-releasing compound from the capsules in the oral cavity, releasing cations from the cation-releasing compound, exposing the mucoadhesive polymer to the cations, and adhering the mucoadhesive polymer to oral surfaces in the oral cavity.

What is claimed is:

1. An aqueous mouthwash comprising:
    a cation-sensitive mucoadhesive polymer; and
    a sequestered cation-releasing compound comprising a soluble divalent salt
    encapsulated in a substantially water-insoluble rupturable capsule to prevent exposure of the cation-sensitive mucoadhesive polymer to the cation-releasing compounds prior to application of a mechanical and/or shear force during application to oral surfaces by the consumer;
    wherein the rupturable capsule comprises silicone.

2. The aqueous mouthwash of claim 1, wherein the mucoadhesive polymer comprises gellan gum.

3. The aqueous mouthwash of claim 1, wherein the mucoadhesive polymer comprises carrageenan.

4. The aqueous mouthwash of claim 1, wherein the cation-releasing compound comprises a calcium salt.

5. The aqueous mouthwash of claim 1, wherein the cation-releasing compound comprises $CaCl_2$.

6. An aqueous mouthwash comprising:
    a cation-sensitive mucoadhesive polymer chosen from the group consisting of gellan gum and carrageenan;
    a $CaCl_2$ salt; and
    a substantially water-insoluble rupturable capsule comprising silicone
    wherein the $CaCl_2$ salt is encapsulated in the rupturable capsule; and wherein the capsule is ruptured upon application of a mechanical and/or shear force.

* * * * *